US011158054B2

(12) United States Patent
Wang

(10) Patent No.: US 11,158,054 B2
(45) Date of Patent: Oct. 26, 2021

(54) MEDICAL IMAGE PROCESSING APPARATUS, MEDICAL IMAGE PROCESSING METHOD, AND MEDICAL IMAGE PROCESSING PROGRAM

(71) Applicant: FUJIFILM Corporation, Tokyo (JP)

(72) Inventor: Caihua Wang, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 124 days.

(21) Appl. No.: 16/792,322

(22) Filed: Feb. 17, 2020

(65) Prior Publication Data

US 2020/0184649 A1 Jun. 11, 2020

Related U.S. Application Data

(63) Continuation of application No. PCT/JP2018/020390, filed on May 28, 2018.

(30) Foreign Application Priority Data

Aug. 28, 2017 (JP) ............................ JP2017-163008

(51) Int. Cl.
*G06K 9/00* (2006.01)
*G06T 7/00* (2017.01)
(Continued)

(52) U.S. Cl.
CPC .......... *G06T 7/0016* (2013.01); *A61B 5/4088* (2013.01); *G06T 7/32* (2017.01);
(Continued)

(58) Field of Classification Search
CPC ........... G06T 7/0016; G06T 7/62; G06T 7/32; G06T 2207/30016; G06T 2207/10072; A61B 5/4088
See application file for complete search history.

(56) References Cited

U.S. PATENT DOCUMENTS

| | | | |
|---|---|---|---|
| 2009/0292551 | A1 | 11/2009 | Sirohey et al. |
| 2017/0024888 | A1 | 1/2017 | Ishii et al. |

(Continued)

FOREIGN PATENT DOCUMENTS

| | | |
|---|---|---|
| JP | 2011010828 | 1/2011 |
| JP | 2014042684 | 3/2014 |

(Continued)

OTHER PUBLICATIONS

"International Search Report (Form PCT/ISA/210) of PCT/JP2018/020390," dated Aug. 21, 2018, with English translation thereof, pp. 1-5.

"Written Opinion of the International Searching Authority (Form PCT/ISA/237) of PCT/JP2018/020390," dated Aug. 21, 2018, with English translation thereof, pp. 1-7.

(Continued)

*Primary Examiner* — Atiba O Fitzpatrick
(74) *Attorney, Agent, or Firm* — JCIPRNET

(57) ABSTRACT

In a medical image processing apparatus, a medical image processing method, and a medical image processing program, in a case where there are a plurality of past brain images, it is possible to select a past brain image with which the atrophy rate of the brain can be accurately calculated. An image acquisition unit acquires a target brain image Bt as a diagnostic target and a plurality of past brain images Bpi, which have earlier imaging dates and times than the target brain image Bt, for the same subject. A similarity calculation unit calculates the similarity between each of the plurality of past brain images Bpi and a standard brain image Bs. A selection unit selects a reference brain image B0 serving as a reference for calculating the amount of change of the brain from the plurality of past brain images Bpi.

20 Claims, 8 Drawing Sheets

1

4

3

2

(51) Int. Cl.

| | |
|---|---|
| ***G06T 7/62*** | (2017.01) |
| ***G06T 7/32*** | (2017.01) |
| ***A61B 5/00*** | (2006.01) |

(52) U.S. Cl.

CPC ...... *G06T 7/62* (2017.01); *G06T 2207/10072* (2013.01); *G06T 2207/30016* (2013.01)

(56) References Cited

U.S. PATENT DOCUMENTS

| | | | |
|---|---|---|---|
| 2017/0206654 | A1 | 7/2017 | Shiroishi et al. |
| 2017/0273650 | A1 | 9/2017 | Ono et al. |

FOREIGN PATENT DOCUMENTS

| | | |
|---|---|---|
| JP | 2016064004 | 4/2016 |
| JP | 2017023457 | 2/2017 |
| JP | 2017124039 | 7/2017 |
| WO | 2015029135 | 3/2015 |

OTHER PUBLICATIONS

Dominic Holland, et al., "Subregional neuroanatomical change as a biomarker for Alzheimer's disease," Proceedings Of The National Academy of Sciences of the United States of America, vol. 106, No. 49, Dec. 8, 2009, p. 20954-20959.

Yakang Dai, et al., "aBEAT: A Toolbox for Consistent Analysis of Longitudinal Adult Brain MRI," PLOS ONE, vol. 8, Apr. 3, 2013, pp. 1-13.

"Search Report of Europe Counterpart Application", dated Sep. 3, 2020, pp. 1-4.

MEDICAL IMAGE PROCESSING APPARATUS, MEDICAL IMAGE PROCESSING METHOD, AND MEDICAL IMAGE PROCESSING PROGRAM

CROSS REFERENCE TO RELATED APPLICATIONS

This application is a Continuation of PCT International Application No. PCT/JP2018/020390 filed on May 28, 2018, which claims priority under 35 U.S.C. § 119(a) to Patent Application No. 2017-163008 filed in Japan on Aug. 28, 2017 all of which are hereby expressly incorporated by reference into the present application.

BACKGROUND OF THE INVENTION

1. Field of the Invention

The present invention relates to a medical image processing apparatus, a medical image processing method, and a non-transitory computer recording medium storing a medical image processing program for calculating the amount of change of a brain due to dementia or the like using brain images that have different imaging dates and times and include the brain for the same subject.

2. Description of the Related Art

With the arrival of an aging society, the number of patients with dementia is increasing year by year. Dementia develops in a case where a protein called amyloid β accumulates in the brain and accordingly brain atrophy progresses and cognitive ability declines. Since there is no cure for dementia, it is important in terms of maintaining the quality of life to detect brain atrophy early and start treatment early to delay the progression of dementia.

In order to meet such a demand, in recent years, information regarding the state of the brain can be acquired by nuclear medicine examinations such as single photon emission computed tomography (SPECT) and positron emission tomography (PET), CT images acquired by computerized tomography (CT) apparatuses, and MRI images acquired by magnetic resonance imaging (MRI) apparatuses. For example, decreased blood flow and metabolism in a local part of the brain can be found by checking a temporal change in the local part of the brain using SPECT and PET images.

On the other hand, brain atrophy can be found by calculating the volume of a specific part of the brain using MRI images and comparing a temporal change in the volume. For example, JP2014-042684A has proposed a method of performing registration between two brain images having different imaging dates and times and then dividing each of the two brain images into tissue regions (gray matter and white matter) and acquiring the amount of change for each tissue region. In addition, a method has also been proposed in which the oldest past medical image as a reference for a certain patient and the current and near past medical images of a specific part of the patient are acquired, a difference between the oldest past image and the current and near past medical images is extracted, and the change rate of the difference with respect to the reference is calculated (refer to JP2015-29135A).

On the other hand, for example, a method of performing registration between a brain image of a patient and a standard brain image region-divided according to the Broadmann's brain map and dividing the brain image of the patient into regions has been proposed (refer to JP2011-010828A). Here, the Broadmann's brain map shows which region in the three-dimensional region of the cerebral cortex of the standard brain controls which brain function (motion, language, perception, memory, vision, hearing, and the like). A method has been proposed in which a brain image of a patient is divided into regions and then the amount of change in the volume for each region is acquired (Subregional neuroanatomical change as a biomarker for Alzheimer's disease, Dominic Holland et al., Proceedings of the National Academy of Sciences, Vol. 106, No. 49, pp. 20954-20959, 2009/12/8 and aBEAT: A Toolbox for Consistent Analysis of Longitudinal Adult Brain MRI, Yakang Dai et al., Alzheimer's Disease Neuroimaging Initiative, Apr. 3, 2013). In the methods described in Subregional neuroanatomical change as a biomarker for Alzheimer's disease, Dominic Holland et al., Proceedings of the National Academy of Sciences, Vol. 106, No. 49, pp. 20954-20959, 2009/12/8 and aBEAT: A Toolbox for Consistent Analysis of Longitudinal Adult Brain MRI, Yakang Dai et al., Alzheimer's Disease Neuroimaging Initiative, Apr. 3, 2013, registration between the first brain image of the patient and the standard brain image is performed to divide the first brain image into regions, and registration between the second brain image of the patient, which has a later imaging date and time than the first brain image, and the standard brain image is performed to divide the second brain image into regions. Then, the amount of change in the volume between corresponding regions in the first brain image and the second brain image is acquired.

SUMMARY OF THE INVENTION

In order to determine the progression of dementia for the same patient, it is necessary to perform registration between the past image of the patient with the current image and accurately calculate the atrophy rate for each region of the brain. On the other hand, in the case of acquiring brain images for the same patient for a plurality of years in order to observe the progress, a plurality of past images are present. In a case where a plurality of past images are present as described above, there is a possibility that the atrophy rate of the brain will change depending on which past image is selected. For example, in a case where an image closest in time to the latest image is selected as a past image, assuming that the brain atrophy has started before the past image, the atrophy rate of the brain from the normal time cannot be accurately calculated. In addition, in a case where the oldest image in time is selected as a past image, the calculated atrophy rate of the brain is a mixture of the atrophy rate due to illness and the normal atrophy rate due to aging. Therefore, when there are a plurality of past images, the atrophy rate of the brain cannot be accurately calculated unless the past image is appropriately selected.

The present invention has been made in view of the above circumstances, and it is an object of the present invention to enable the selection of a past brain image, with which the atrophy rate of the brain can be accurately calculated, in a case where there are a plurality of past brain images.

A medical image processing apparatus according to the present invention comprises: an image acquisition unit that acquires a target brain image as a diagnostic target and a plurality of past brain images, which have earlier imaging dates and times than the target brain image, for the same subject; a similarity calculation unit that calculates a similarity between each of the plurality of past brain images and a standard brain image; and a selection unit that selects a past brain image, which has the similarity equal to or greater than a predetermined threshold value and has an imaging date and time closest to a current date and time, as a reference brain image from the plurality of past brain images.

In the medical image processing apparatus according to the present invention, the similarity calculation unit may calculate a similarity between each of a plurality of standard brain images and each of the plurality of past brain images.

In the medical image processing apparatus according to the present invention, the similarity calculation unit may perform registration between each of the plurality of past brain images and the standard brain image and calculate a correlation between the standard brain image and each of the plurality of past brain images after the registration as the similarity.

Here, the shape and size of the brain vary from subject to subject. "A plurality of standard brain images" means a plurality of standard brain images having different shapes and sizes.

The medical image processing apparatus according to the present invention may further comprise a change amount calculation unit that calculates an amount of change of a brain based on the target brain image and the reference brain image.

In the medical image processing apparatus according to the present invention, the change amount calculation unit may comprise: a division unit that divides a brain included in the target brain image into a plurality of regions by performing registration between the target brain image and the standard brain image; a registration unit that performs registration between the target brain image and the reference brain image; and a change amount acquisition unit that acquires an amount of change from a corresponding region in a brain included in the reference brain image, for at least one region of the plurality of regions in a brain included in the target brain image, based on a result of registration between the target brain image and the reference brain image.

In the medical image processing apparatus according to the present invention, the change amount acquisition unit may calculate a volume change amount from a corresponding region of the reference brain image for at least one region of the plurality of regions in the brain included in the target brain image.

The medical image processing apparatus according to the present invention may further comprise a display control unit that displays the volume change amount on a display unit.

In the medical image processing apparatus according to the present invention, the registration unit may acquire a movement vector between corresponding pixel positions as the amount of change between corresponding regions of the brain included in the target brain image and the brain included in the reference brain image.

In the medical image processing apparatus according to the present invention, the division unit may perform second registration between the target brain image and the standard brain image after performing first registration using landmarks between the target brain image and the standard brain image.

A "landmark" is a region having a characteristic shape in the target brain image and the standard brain image. Specifically, at least one of characteristic regions, such as a sulcus and a cerebral ventricle included in the brain, can be used as a landmark.

In this case, the first registration may be registration by similarity transformation, and the second registration may be registration by nonlinear transformation.

In the medical image processing apparatus according to the present invention, the registration unit may perform fourth registration between the target brain image and the reference brain image after performing third registration using landmarks between the target brain image and the reference brain image.

In this case, the third registration may be rigid registration, and the fourth registration may be registration by nonlinear transformation.

The third registration is registration using landmarks, but the fourth registration is registration using any regions between the target brain image and the reference brain image. The registration using any region may be, for example, registration using the entire region between the target brain image and the reference brain image or registration using only a partial region.

A medical image processing method according to the present invention comprises: acquiring a target brain image as a diagnostic target and a plurality of past brain images, which have earlier imaging dates and times than the target brain image, for the same subject; calculating a similarity between each of the plurality of past brain images and a standard brain image; and selecting a past brain image, which has the similarity equal to or greater than a predetermined threshold value and has an imaging date and time closest to a current date and time, as a reference brain image from the plurality of past brain images.

In addition, a non-transitory computer recording medium storing a program causing a computer to execute the medical image processing method according to the present invention may be provided.

Another medical image processing apparatus according to the present invention comprises: a memory that stores commands to be executed by a computer; and a processor configured to execute the stored commands. The processor executes processing for acquiring a target brain image as a diagnostic target and a plurality of past brain images, which have earlier imaging dates and times than the target brain image, for the same subject; calculating a similarity between each of the plurality of past brain images and a standard brain image; and selecting a past brain image, which has the similarity equal to or greater than a predetermined threshold value and has an imaging date and time closest to a current date and time, as a reference brain image from the plurality of past brain images.

According to the present invention, a target brain image as a diagnostic target and a plurality of past brain images, which have earlier imaging dates and times than the target brain image, for the same subject are acquired, and the similarity between each of the plurality of past brain images and the standard brain image is calculated. Then, a past brain image, which has a similarity equal to or greater than the predetermined threshold value and has an imaging date and time closest to the current date and time, is selected as the reference brain image from the plurality of past brain images. The reference brain image selected in this manner is captured at the date and time closest in time to the target brain image, but has a shape and size close to the standard brain image. For this reason, the reference brain image is acquired at the date and time closest to the date and time at which size and shape changes began among the plurality of past brain images. Therefore, the amount of change of the brain calculated using the target brain image and the reference brain image indicates the amount of change of the brain with a substantially normal point in time as a reference. Therefore, according to the present invention, in a case where there are a plurality of past brain images, a past brain image with which the atrophy rate of the brain can be accurately calculated can be selected as the reference brain image.

DESCRIPTION OF THE PREFERRED EMBODIMENTS

Figure 1:
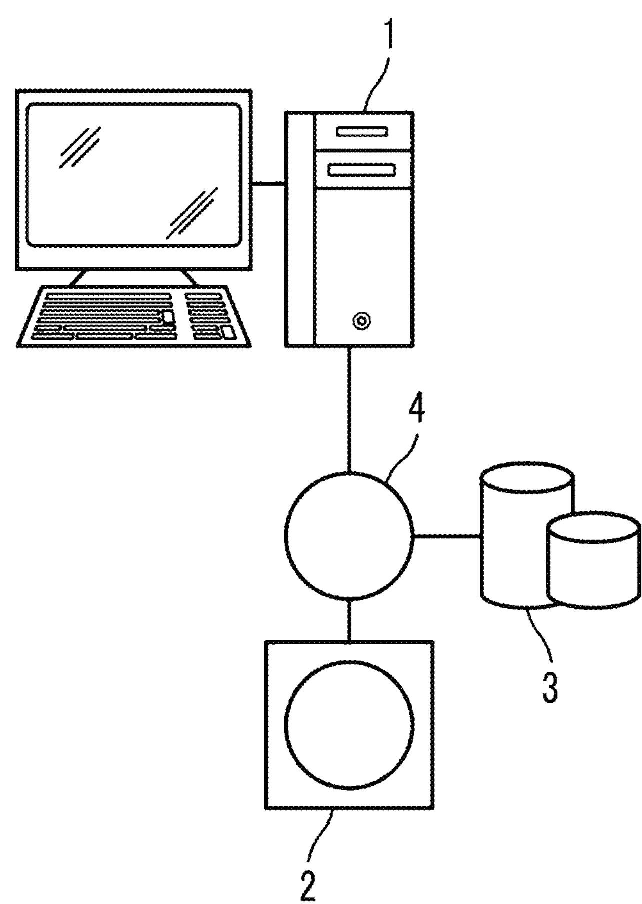
FIG. 1 is a hardware configuration diagram showing an outline of a diagnostic support system to which a medical image processing apparatus according to an embodiment of the present invention is applied.

Hereinafter, an embodiment of the present invention will be described with reference to the accompanying diagrams. FIG. 1 is a hardware configuration diagram showing the outline of a diagnostic support system to which a medical image processing apparatus according to an embodiment of the present invention is applied. As shown in FIG. 1, in the diagnostic support system, a medical image processing apparatus 1 according to the present embodiment, a three-dimensional image capturing apparatus 2, and an image storage server 3 are communicably connected to each other through a network 4.

The three-dimensional image capturing apparatus 2 is an apparatus that generates a three-dimensional image showing a part, which is a diagnostic target part of a patient who is a subject, as a medical image by imaging the part. Specifically, the three-dimensional image capturing apparatus 2 is a CT apparatus, an MRI apparatus, a PET apparatus, or the like. The medical image generated by the three-dimensional image capturing apparatus 2 is transmitted to the image storage server 3 and is stored therein. In the present embodiment, a diagnostic target part of a patient who is a subject is a brain, the three-dimensional image capturing apparatus 2 is an MRI apparatus, and an MRI image of the head including the brain of the subject is generated as a three-dimensional brain image.

The image storage server 3 is a computer that stores and manages various kinds of data, and comprises a large-capacity external storage device and software for database management. The image storage server 3 communicates with other apparatuses through the wired or wireless network 4 to transmit and receive image data or the like. Specifically, the image storage server 3 acquires various kinds of data including image data of the medical image, which is generated by the three-dimensional image capturing apparatus 2, through the network, and stores the acquired data in a recording medium, such as a large-capacity external storage device, to manage the acquired data. The storage format of image data and the communication between devices through the network 4 are based on a protocol, such as a digital imaging and communication in medicine (DICOM). In the present embodiment, it is assumed that image data of a plurality of three-dimensional brain images having different imaging dates and times for the same subject are stored in the image storage server 3. In addition, it is assumed that image data of a standard brain image to be described later is also stored in the image storage server 3.

The medical image processing apparatus 1 is realized by installing a medical image processing program of the present invention on one computer. The computer may be a workstation or a personal computer that is directly operated by a doctor who performs diagnosis, or may be a server computer connected to these through a network. The medical image processing program is distributed in a state in which the medical image processing program is recorded on a recording medium, such as a digital versatile disc (DVD) or a compact disc read only memory (CD-ROM), and is installed onto the computer from the recording medium. Alternatively, the medical image processing program is stored in a storage device of a server computer connected to the network or in a network storage so as to be accessible from the outside, and is downloaded and installed onto a computer used by a doctor as necessary.

Figure 2:
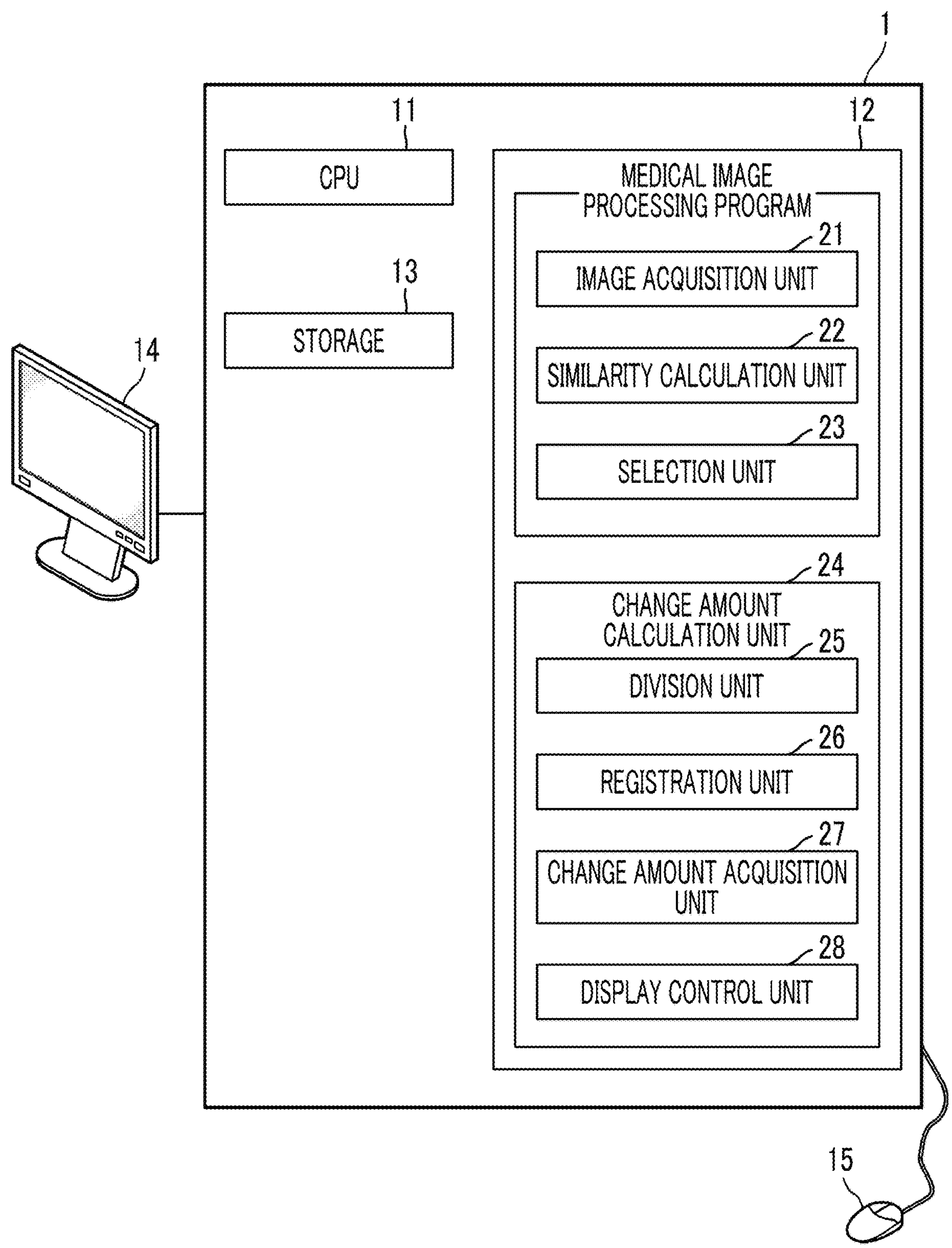
FIG. 2 is a diagram showing the schematic configuration of the medical image processing apparatus.

FIG. 2 is a diagram showing the schematic configuration of a medical image processing apparatus realized by installing a medical image processing program on a computer. As shown in FIG. 2, the medical image processing apparatus 1 comprises a central processing unit (CPU) 11, a memory 12, and a storage 13 as the configuration of a standard workstation. A display 14, such as a liquid crystal display, and an input unit 15, such as a keyboard and a mouse, are connected to the medical image processing apparatus 1. The display 14 corresponds to a display unit.

The storage 13 is a recording medium, such as a hard disk drive or a solid state drive (SSD), and stores a plurality of brain images having different imaging dates and times for the same subject, a standard brain image to be described later, and various kinds of information including information necessary for processing, which are acquired from the image storage server 3 through the network 4.

A medical image processing program is stored in the memory 12. As processing to be executed by the CPU 11, the medical image processing program defines: image acquisition processing for acquiring a target brain image as a diagnostic target and a plurality of past brain images, which have earlier imaging dates and times than the target brain image, for the same subject; similarity calculation processing for calculating a similarity between each of the plurality of past brain images and a standard brain image; selection processing for selecting a past brain image, which has the similarity equal to or greater than a predetermined threshold value and has an imaging date and time closest to a current date and time, as a reference brain image from the plurality of past brain images; and change amount calculation processing for calculating an amount of change of a brain based on the target brain image and the reference brain image.

In addition, as the change amount calculation processing, the medical image processing program defines: division processing for dividing a brain included in the target brain image into a plurality of regions by performing registration between the target brain image and the standard brain image; registration processing for performing registration between the target brain image and the reference brain image; change amount acquisition processing for acquiring an amount of change from a corresponding region in a brain included in the reference brain image, for at least one region of the plurality of regions in a brain included in the target brain image, based on a result of registration between the target brain image and the reference brain image; and display control processing for displaying the amount of change amount on the display 14.

The CPU 11 executes these processes according to the program, so that the computer functions as an image acquisition unit 21, a similarity calculation unit 22, a selection unit 23, a change amount calculation unit 24, a division unit 25, a registration unit 26, a change amount acquisition unit 27, and a display control unit 28. The medical image processing apparatus 1 may comprise a plurality of processors or processing circuits that perform image acquisition processing, similarity calculation processing, selection processing, change amount calculation processing, division processing in change amount calculation processing, registration processing, change amount acquisition processing, and display control processing.

The image acquisition unit 21 acquires a target brain image Bt as a diagnostic target and a plurality of past brain images Bpi (i is 2 or more), which have earlier imaging dates and times than the target brain image Bt, for the same subject from the image storage server 3. In a case where the target brain image Bt and the plurality of past brain images Bpi are already stored in the storage 13, the image acquisition unit 21 may acquire the target brain image Bt and the plurality of past brain images Bpi from the storage 13. The target brain image Bt is the latest brain image of the subject, but is not limited to this as long as the target brain image Bt has a later imaging date and time than the plurality of past brain images Bpi. In the present embodiment, those stored in the image storage server 3 are brain images acquired by imaging the head of the subject, and include structures other than the brain, such as a skull. The image acquisition unit 21 also acquires a standard brain image Bs from the image storage server 3.

The standard brain image Bs is a three-dimensional brain image showing a brain having a standard shape and size and a standard density (pixel value), that is, a standard brain. The standard brain image Bs can be generated by extracting brains from a plurality of brain images, which are acquired by imaging the heads of a plurality of healthy persons with a three-dimensional image capturing apparatus, and averaging the plurality of extracted brains. The standard brain image Bs may be created by computer graphics or the like. Alternatively, a brain image of one healthy person may be used as the standard brain image Bs.

Figure 3:
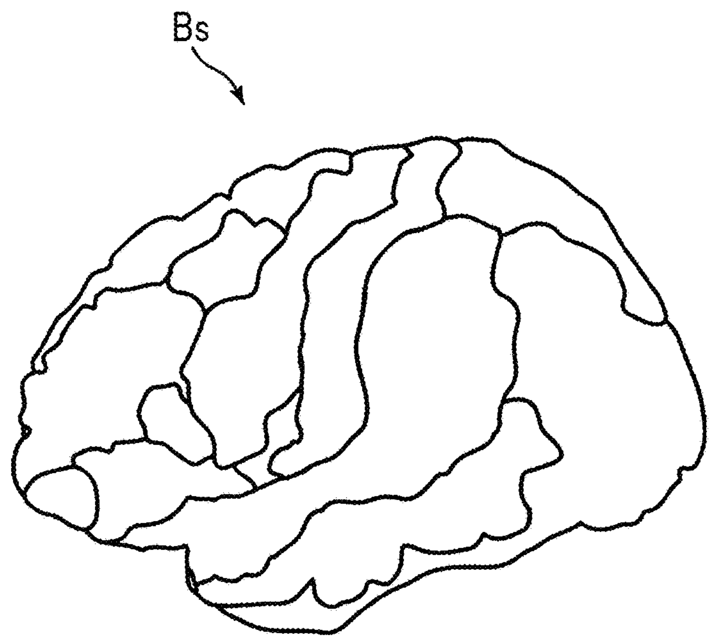
FIG. 3 is a diagram showing a standard brain image.

In the present embodiment, the standard brain image Bs is divided into a plurality of regions. As a method of division, for example, based on the Broadmann's brain map, within the three-dimensional region of the cerebral cortex, it is possible to use a method of dividing the cerebral cortex into regions responsible for functions, such as movement, language, perception, memory, vision sense, and acoustic sense. In addition, it is possible to use any known method, such as a method for division into six kinds of regions of cerebrum, diencephalon, mesencephalon, hindbrain, cerebellum, and medulla oblongata and a method of dividing the cerebrum into frontal lobe, parietal lobe, temporal lobe, and occipital lobe. Alternatively, a method of simply dividing the brain at equal intervals may be used. FIG. 3 is a diagram showing an example of a standard brain image. In FIG. 3, the standard brain image Bs is divided into a plurality of regions according to Brodmann's brain map.

The similarity calculation unit 22 calculates the similarity between each of the plurality of past brain images Bpi and the standard brain image Bs. Specifically, the similarity calculation unit 22 performs registration between each of the plurality of past brain images Bpi and the standard brain image Bs, and calculates the correlation between the standard brain image Bs and each of the plurality of past brain images Bpi after the registration as a similarity Si. Here, as the registration, rigid registration for parallel movement, rotation, and similar enlargement and reduction of the standard brain image Bs or the past brain image Bpi can be used. As the correlation, it is possible to use the sum of absolute values of difference values between corresponding pixels of the standard brain image Bs and the past brain image Bpi after the registration, the sum of squares of the difference values, and the like. The method of calculating the similarity Si is not limited to this. For example, the correlation between the histogram of pixel values in the corpus callosum region of the past brain image Bpi and the histogram of pixel values in the corpus callosum region of the standard brain image Bs may be calculated as the similarity Si. In addition, any method other than this can be used as the method of calculating the similarity Si.

The selection unit 23 selects a reference brain image B0 serving as a reference for calculating the amount of change of the brain from the plurality of past brain images Bpi.

Figure 4:
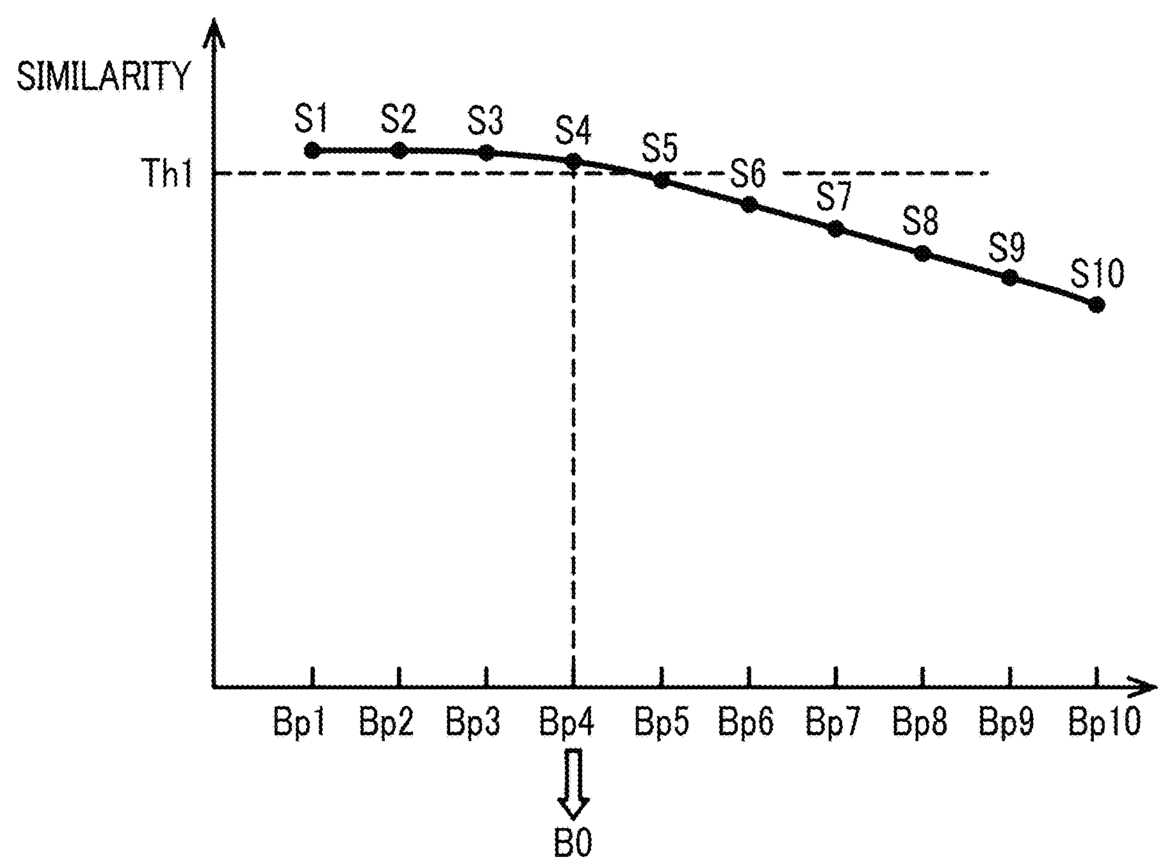
FIG. 4 is a diagram illustrating the selection of a reference brain image.

FIG. 4 is a diagram illustrating the selection of the reference brain image B0. Here, it is assumed that ten past brain images Bp1 to Bp10 are acquired and ten similarities S1 to S10 are calculated. In addition, it is assumed that the past brain images Bp1 to Bp10 have earlier imaging dates and times as the given number is smaller. In FIG. 4, the horizontal axis indicates the date and time, and the vertical axis indicates the similarity. Here, the brain of a patient with dementia atrophies with time. For this reason, the similarity between each of the past brain images Bp1 to Bp10 and the standard brain image Bs becomes smaller as the imaging date and time becomes later. On the other hand, in the past brain images with earlier imaging dates and times, in a case where the atrophy of the brain due to dementia has not started, only the atrophy of the brain due to aging is included. Therefore, the similarity with the standard brain image Bs is relatively large and hardly changes with time. In order to accurately calculate the atrophy of the brain due to dementia, it is important to perform comparison with a past brain image at the time at which a large change in the brain, that is, larger atrophy than aged atrophy began.

The selection unit 23 selects a past brain image, which has the similarity Si equal to or greater than a predetermined threshold value Th1 and has an imaging date and time closest to the current date and time, as the reference brain image B0 from the plurality of past brain images Bpi. For example, in a case where the similarities S1 to S10 calculated for the past brain images Bp1 to Bp10 change as shown in FIG. 4, the similarities S1 to S4 of the past brain images Bp1 to Bp4 are larger than the threshold value Th1. Among the past brain images Bp1 to Bp4, a brain image having an imaging date and time closest to the imaging date and time of the target brain image Bt, that is, the latest brain image is the past brain image Bp4. Therefore, the selection unit 23 selects the past brain image Bp4 as the reference brain image B0.

The change amount calculation unit 24 calculates the amount of change of the brain based on the target brain image Bt and the reference brain image B0. Hereinafter, the calculation of the amount of change will be described.

In order to calculate the amount of change of the brain, the division unit 25 of the change amount calculation unit 24 divides the brain included in the target brain image Bt into a plurality of regions by performing registration between the target brain image Bt and the standard brain image Bs.

Figure 5:
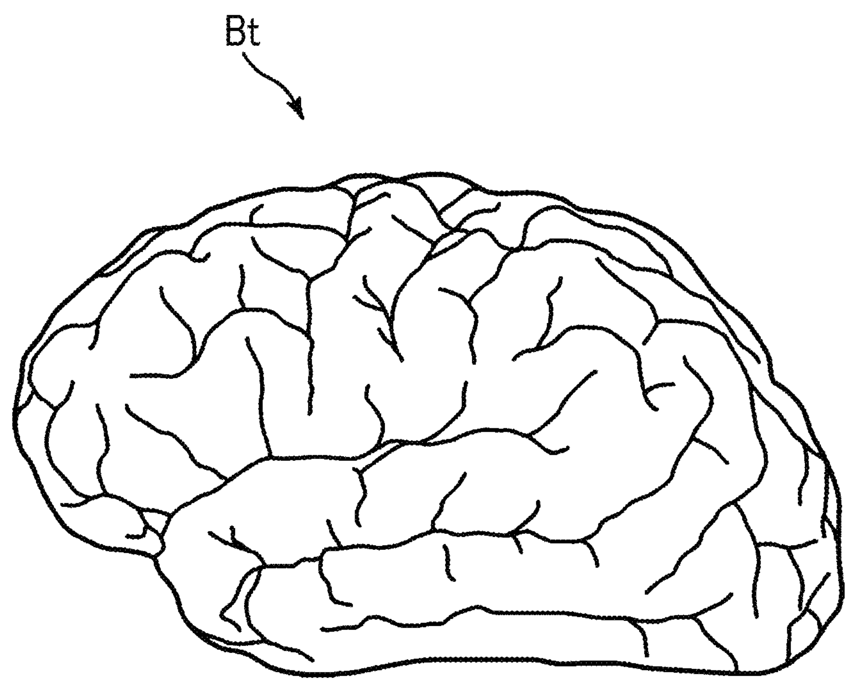
FIG. 5 is a diagram showing a target brain image.

The size and shape of the brain vary from person to person. For example, in a case where the brain is compared with the standard brain, the size and shape of the brain are different by about ±15% at the maximum. FIG. 5 is a diagram showing the target brain image Bt. As shown in FIG. 5, the target brain image Bt has a different shape and size from the standard brain image Bs shown in FIG. 3. In order to divide the target brain image Bt into a plurality of regions, the division unit 25 performs first registration using landmarks between the target brain image Bt and the standard brain image Bs. Then, after performing the first registration, second registration using the entire region is performed between the target brain image Bt and the standard brain image Bs. As a landmark, specifically, at least one of characteristic regions, such as a sulcus and a cerebral ventricle included in the brain, can be used. In the present embodiment, the following description will be given on the assumption that the standard brain image Bs is registrated with the target brain image Bt. However, the target brain image Bt may be registrated with the standard brain image Bs.

For registration, the division unit 25 extracts landmarks from the target brain image Bt and the standard brain image Bs. For example, landmarks may be extracted by template matching using a template indicating a landmark, or may be extracted using a discriminator that has been learned to discriminate landmarks included in an image. The division unit 25 performs the first registration between the target brain image Bt and the standard brain image Bs so that the corresponding landmarks match each other. In the present embodiment, the first registration is registration by similarity transformation. Specifically, the first registration is registration by parallel movement, rotation, and similar enlargement and reduction of the standard brain image Bs. The division unit 25 performs the first registration by performing similarity transformation of the standard brain image Bs so that the correlation between the landmark included in the standard brain image Bs and the corresponding landmark included in the target brain image Bt is maximized.

After performing the first registration using the landmark as described above, the division unit 25 performs the second registration using the entire region between the target brain image Bt and the standard brain image Bs. In the present embodiment, the second registration is registration by nonlinear transformation. As the registration by nonlinear transformation, for example, there is registration performed by nonlinearly converting pixel positions using functions, such as B spline and thin plate spline. The division unit 25 performs the second registration by nonlinearly converting each pixel position of the standard brain image Bs after the first registration to a corresponding pixel position included in the target brain image Bt.

Figure 6:
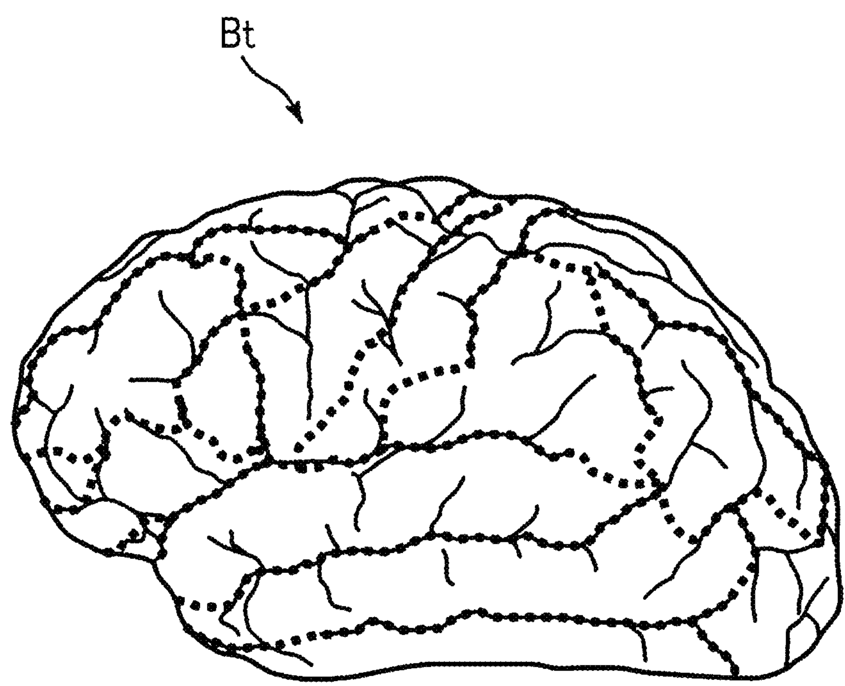
FIG. 6 is a diagram showing a target brain image divided into a plurality of regions.

By registrating the standard brain image Bs with the target brain image Bt as described above and applying the boundary between divided regions in the standard brain image Bs to the target brain image Bt, the division unit 25 divides the target brain image Bt into a plurality of regions as shown in FIG. 6.

The registration unit 26 of the change amount calculation unit 24 performs registration between the target brain image Bt and the reference brain image B0. Specifically, after performing third registration using the landmarks between the target brain image Bt and the reference brain image B0, fourth registration using the entire region is performed between the target brain image Bt and the reference brain image B0. Although the present embodiment has been described given on the assumption that the target brain image Bt is registrated with the reference brain image B0, reference brain image B0 may be registrated with the target brain image Bt.

For registration, the registration unit 26 extracts landmarks from the target brain image Bt and the reference brain image B0. The landmark extraction may be performed in the same manner as the first registration described above. The registration unit 26 performs the third registration between the target brain image Bt and the reference brain image B0 so that the corresponding landmarks match each other. Here, the brain included in the target brain image Bt and the brain included in the reference brain image B0 have the same size since the subject is the same. Therefore, in the present embodiment, rigid registration using only parallel movement and rotation is performed as the third registration.

Figure 7:
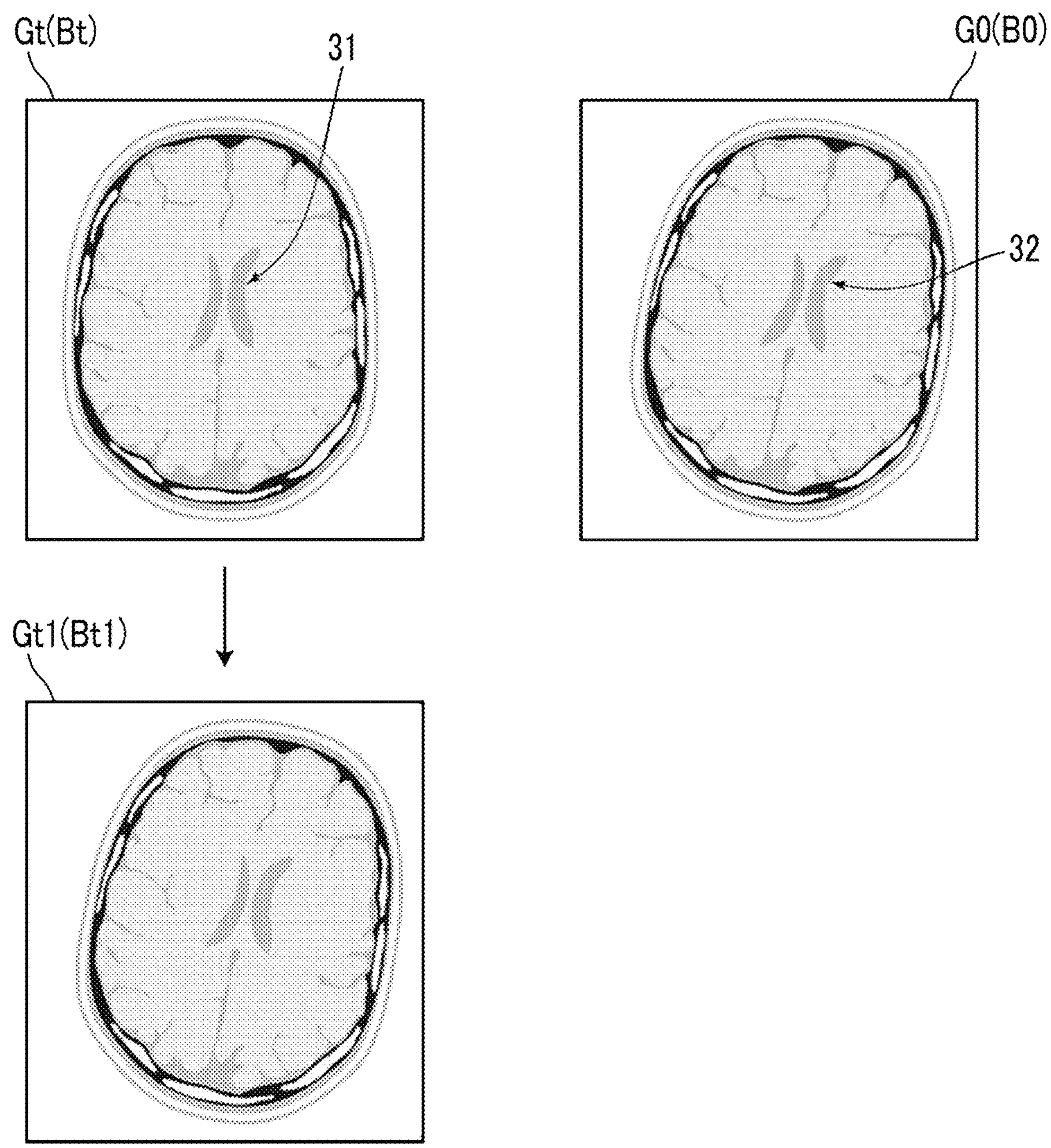
FIG. 7 is a diagram illustrating registration.

FIG. 7 is a diagram illustrating rigid registration. In FIG. 7, for the sake of description, slice images Gt and G0 of the corresponding tomographic planes in the target brain image Bt and the reference brain image B0 are shown. As shown in FIG. 7, the registration unit 26 performs the third registration, which is rigid registration, by performing parallel movement and rotation of the target brain image Bt so that the correlation between a cerebral ventricle 31, which is one of the landmarks of the slice image Gt of the target brain image Bt, and a corresponding cerebral ventricle 32 included in the slice image G0 of the reference brain image B0 is maximized. Therefore, a target brain image Bt1 (in FIG. 7, a slice image Gt1) subjected to the third registration is acquired.

Figure 8:
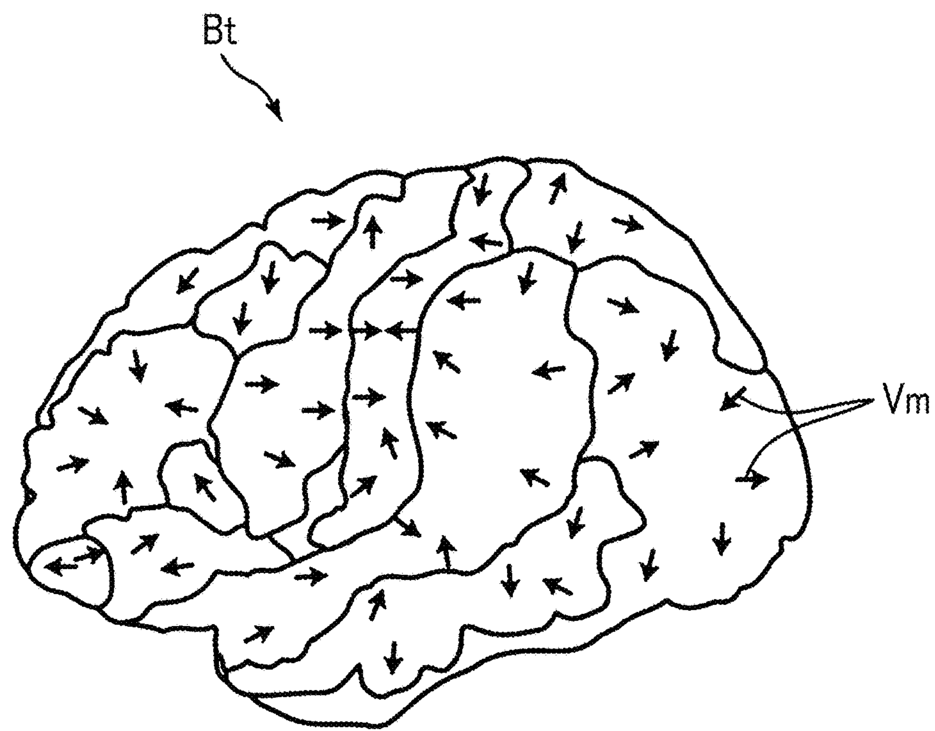
FIG. 8 is a diagram showing a movement vector.

After performing the third registration using the landmark as described above, the registration unit 26 performs the fourth registration using the entire region between the target brain image Bt and the reference brain image B0. In the present embodiment, the fourth registration is registration by nonlinear transformation. The fourth registration may be performed in the same manner as the second registration described above. Therefore, a movement vector of each pixel of the target brain image Bt to the corresponding pixel position of the reference brain image B0 is acquired. FIG. 8 is a diagram showing a movement vector. As shown in FIG. 8, a movement vector Vm is acquired at each pixel position of the brain in the target brain image Bt.

The change amount acquisition unit 27 of the change amount calculation unit 24 acquires the amount of change from a corresponding region in the brain included in the reference brain image B0, for at least one region of the plurality of regions in the brain included in the target brain image Bt, based on the registration result of the registration unit 26. In the present embodiment, it is assumed that the amount of change for each of a plurality of regions is acquired. In the present embodiment, the movement vector Vm is acquired at each pixel position of the brain included in the target brain image Bt by the registration of the registration unit 26. The change amount acquisition unit 27 classifies the movement vector Vm at each pixel position of the brain included in the target brain image Bt into a plurality of regions in the target brain image Bt. Therefore, for each of the plurality of regions in the brain included in the target brain image Bt, the amount of change from a corresponding region in the brain included in the reference brain image B0 is acquired. In this case, the amount of change is the movement vector Vm of a corresponding pixel in a corresponding region. In addition, the change amount acquisition unit 27 calculates a volume change amount for each of the plurality of regions in the brain included in the target brain image Bt.

Figure 9:
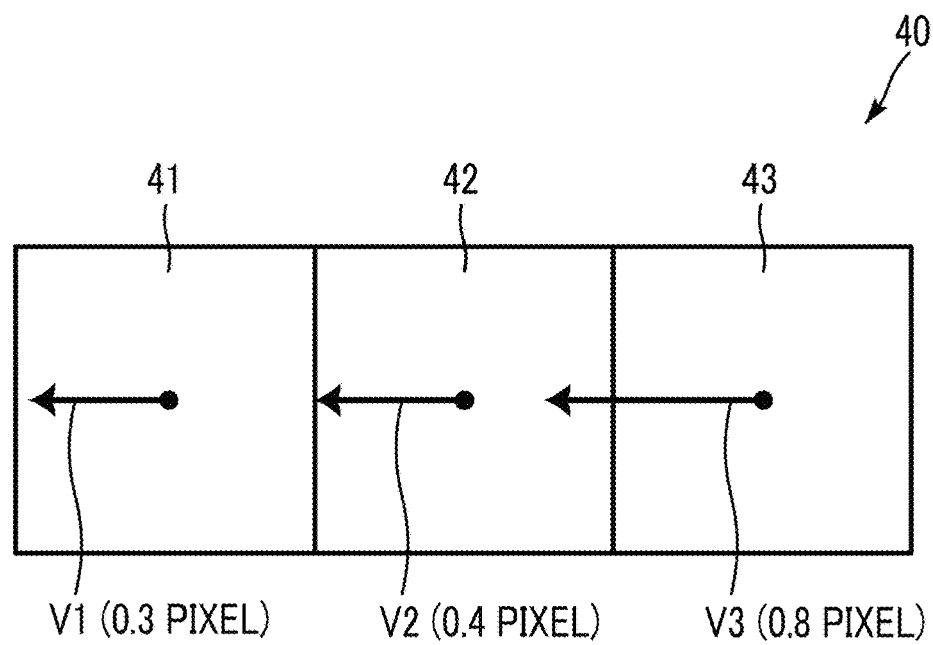
FIG. 9 is a diagram illustrating the calculation of a volume change amount.

FIG. 9 is a diagram illustrating the calculation of the volume change amount. Here, for the sake of description, it is assumed that one region 40 included in the target brain image Bt includes three pixels 41, 42, and 43 and the pixels have not moved in the vertical direction in FIG. 9. In a region A1 configured to include the three pixels 41, 42, and 43 in the target brain image Bt, it is assumed that a movement vector V1 of the pixel 41 has a size of 0.3 pixel in the left direction, a movement vector V2 of the pixel 42 has a size of 0.4 pixel in the left direction, and a movement vector V3 of the pixel 43 has a size of 0.8 pixel in the left direction.

In this case, the entire region 40 is moved to the left. The interval between the pixel 41 and the pixel 42 is reduced by 0.1 pixel. The interval between the pixel 42 and the pixel 43 is reduced by 0.4 pixel. Therefore, the change amount acquisition unit 27 calculates the amount of change in the pixel value of each region 40 as −0.5 pixel. In practice, the change amount acquisition unit 27 calculates the amount of change in the pixel value in each of the directions of the three axes of x, y, and z for each region in the target brain image Bt. The region atrophies in a case where the amount of change is a negative value, and expands in a case where the amount of change is a positive value.

The change amount acquisition unit 27 further calculates a volume change amount as follows. That is, for each region in the target brain image Bt, the amount of change calculated for each of the directions of the three axes of x, y, and z is added. Then, by dividing the added value obtained in this manner by the total number of pixels in the corresponding region, the volume change rate of the region is calculated as the volume change amount. In this case, the volume change amount is expressed as a change rate (for example, percentage) with respect to the volume of each region. The volume change amount is also a negative value in a case where the region atrophies, and is a positive value in a case where the region expands. Here, the absolute value of the volume change amount, which is a negative value, is the atrophy rate of the brain.

For each region in the target brain image Bt, an added value obtained by adding the amount of change calculated for each of the directions of the three axes of x, y, and z may be calculated as the volume change amount. In this case, the volume change amount is expressed by the magnitude of the pixel value, and the volume change amount is a negative value in a case where the region atrophies and is a positive value in a case where the region expands.

In the target brain image Bt and the reference brain image B0, the volume per pixel (that is, one voxel) is known in advance. For this reason, the amount of change calculated for each of the directions of the three axes of x, y, and z may be added, and the volume change amount may be calculated by multiplying the added value obtained in this manner by the volume per pixel. In this case, the volume change amount is expressed by the magnitude of the amount of change in the volume.

The change amount acquisition unit 27 compares the absolute value of the volume change amount, that is, the atrophy rate of the brain with a predetermined threshold value Th2 for a region having a negative value, and specifies a region having an absolute value of the volume change amount larger than the threshold value Th2 as an abnormal region and assigns a label. Here, the atrophy rate of the brain due to human aging is less than 1% per year, but is about 1% to 3% in the case of a patient with dementia. For this reason, the change amount acquisition unit 27 sets, for example, the threshold value Th2 to −1%, and specifies a region having an absolute value of the volume change amount larger than the threshold value Th2 as an abnormal region.

Figure 10:
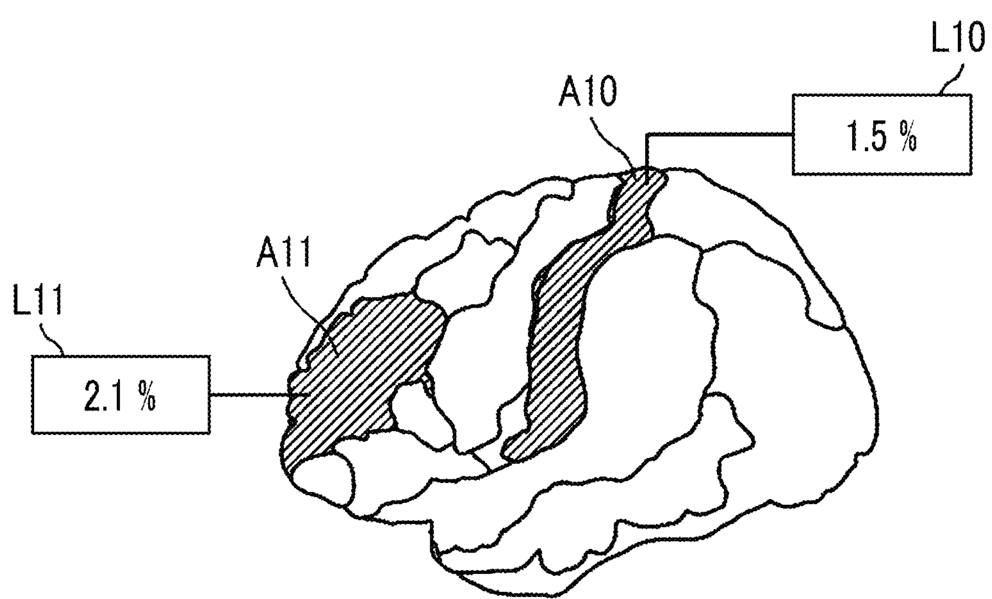
FIG. 10 is a diagram illustrating the display of a volume change amount.

The display control unit 28 of the change amount calculation unit 24 displays the volume change amount on the display 14. FIG. 10 is a diagram illustrating the display of the volume change amount. As shown in FIG. 10, on the display 14, diagonal lines are given to abnormal regions A10 and A11 among the plurality of regions of the brain, and labels L10 and L11 indicating the volume change amount are given thereto. In FIG. 10, the labels L10 and L11 indicate the absolute value of the volume change amount, that is, the atrophy rate of the brain. Each region may be displayed in different colors according to the magnitude of the volume change amount. In the present embodiment, the display control unit 28 is configured as a part of the change amount calculation unit 24. However, the change amount calculation unit 24 may be provided separately from the display control unit 28.

Here, a region determined to have a large amount of change in the brain, that is, a large atrophy rate is displayed in an identifiable manner on the assumption that a doctor makes a diagnosis. However, the presence or absence of the occurrence of dementia may be automatically determined, and the result may be displayed. In this case, a discriminator is created by performing machine learning for a plurality of past patients using the amount of change for each region, that is, the atrophy rate and the presence or absence of the occurrence of dementia as teacher data (data with correct answers). Then, the amount of change, that is, the atrophy rate for each region of a new patient calculated in the present embodiment may be input to the discriminator to determine whether or not the new patient has dementia.

Figure 11:
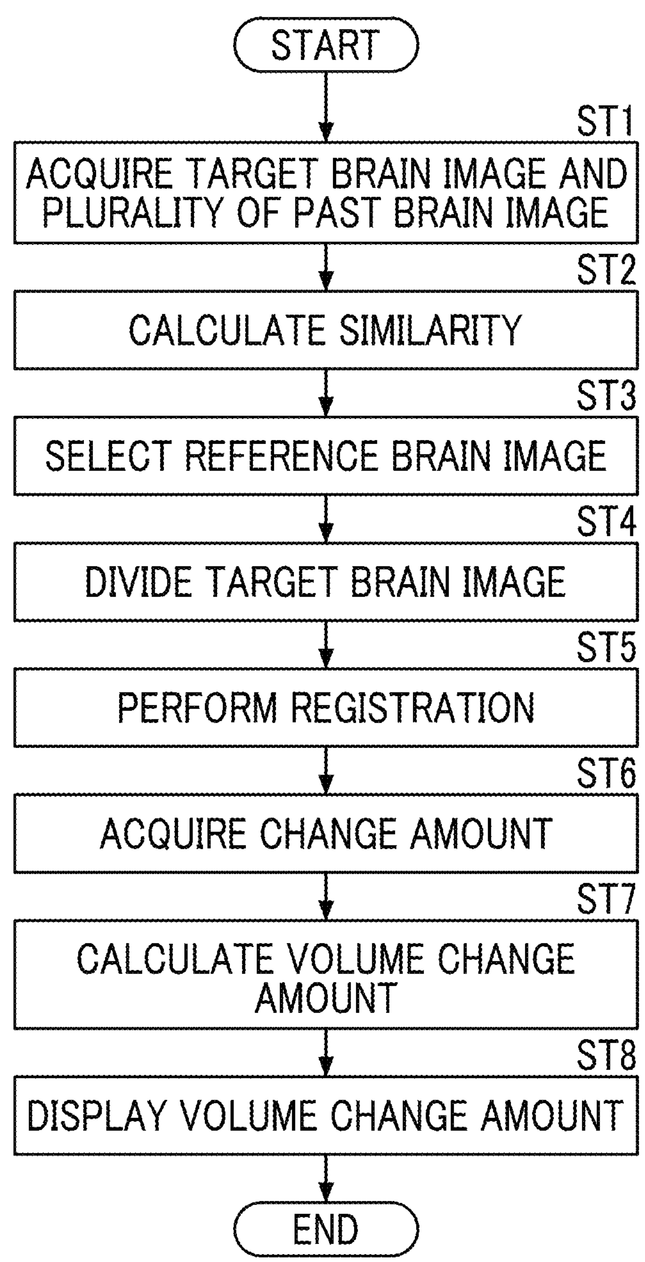
FIG. 11 is a flowchart showing the process performed in the present embodiment.

Next, a process performed in the present embodiment will be described. FIG. 11 is a flowchart showing the process performed in the present embodiment. First, the image acquisition unit 21 acquires the target brain image Bt as a diagnostic target and a plurality of past brain images Bpi, which have earlier imaging dates and times than the target brain image Bt, for the same subject (step ST1). Then, the similarity calculation unit 22 calculates the similarity between each of the plurality of past brain images Bpi and the standard brain image Bs (step ST2). Then, the selection unit 23 selects the reference brain image B0 serving as a reference for calculating the amount of change of the brain from the plurality of past brain images Bpi (step ST3).

Then, the division unit 25 of the change amount calculation unit 24 divides the brain included in the target brain image Bt into a plurality of regions by performing registration between the target brain image Bt and the standard brain image Bs divided into a plurality of regions (step ST4). Then, the registration unit 26 of the change amount calculation unit 24 performs registration between the target brain image Bt and the reference brain image B0 (step ST5).

Then, the change amount acquisition unit 27 of the change amount calculation unit 24 acquires the amount of change from a corresponding region in the brain included in the reference brain image B0, for at least one region of the plurality of regions in the brain included in the target brain image Bt, based on the registration result (step ST6). Then, the change amount acquisition unit 27 of the change amount calculation unit 24 calculates a volume change amount from the corresponding region of the reference brain image B0 for at least one region of the plurality of regions in the brain included in the target brain image Bt (step ST7). Then, the display control unit 28 of the change amount calculation unit 24 displays the volume change amount on the display 14 (step ST8), and the process is ended.

As described above, in the present embodiment, the target brain image Bt as a diagnostic target and the plurality of past brain images Bpi for the same subject are acquired, and the similarity Si between each of the plurality of past brain images Bpi and the standard brain image Bs is calculated. Then, a past brain image, which has the similarity Si equal to or greater than the predetermined threshold value Th1 and has an imaging date and time closest to the current date and time, is selected as the reference brain image B0 from the plurality of past brain images Bpi. The reference brain image B0 selected in this manner is captured at the date and time closest in time to the target brain image Bt, but has a shape and size close to the standard brain image Bs. For this reason, the reference brain image B0 is acquired at the date and time closest to the date and time at which size and shape changes began among the plurality of past brain images Bpi. Therefore, the amount of change of the brain calculated using the target brain image Bt and the reference brain image B0 indicates the amount of change of the brain with a substantially normal point in time as a reference. Therefore, according to the present embodiment, in a case where there are a plurality of past brain images, a past brain image with which the atrophy rate of the brain can be accurately calculated can be selected as the reference brain image B0.

The shape and size of the brain of the subject differ depending on the age, physique, and the like. For this reason, in the case of calculating the similarity between the past brain image Bpi and the standard brain image Bs, the similarity calculation unit 22 may calculate the similarities with a plurality of standard brain images Bs having different shapes and sizes. In this case, a plurality of standard brain images Bs having different shapes and sizes may be stored in the storage 13. As described above, by calculating the similarities with a plurality of standard brain images Bs having different shapes and sizes, it is possible to calculate the similarity with the standard brain images Bs having an appropriate shape and size according to the subject. Therefore, it is possible to select the reference brain image B0 that is more suitable for calculating the atrophy rate of the brain.

In the embodiment described above, rigid registration is performed as the third registration. However, the target brain image Bt and the reference brain image B0 may include brains having different sizes. In such a case, as the third registration, enlargement and reduction may be performed in addition to the rigid registration.

In the embodiment described above, the volume change amount is calculated. However, only the amount of change of each region may be calculated.

In the embodiment described above, the division unit 25 of the change amount calculation unit 24 performs the second registration after performing the first registration using the landmarks. However, only the second registration, that is, registration by nonlinear transformation may be performed.

In the embodiment described above, the registration unit 26 of the change amount calculation unit 24 performs the fourth registration after performing the third registration using the landmarks. However, only the fourth registration, that is, registration by nonlinear transformation may be performed.

In the embodiment described above, registration using the entire regions of the standard brain image Bs and the target brain image Bt is performed as the second registration in the division unit 25. However, registration using the regions of parts of the standard brain image Bs and the target brain image Bt may be performed. For example, registration may be performed using only individual divided regions in the brain.

In the embodiment described above, registration using the entire regions of the target brain image Bt and the reference brain image B0 is performed as the fourth registration in the registration unit 26. However, registration using the regions of parts of the target brain image Bt and the reference brain image B0 may be performed. For example, registration may be performed using only individual divided regions in the brain.

In the embodiment described above, the MM image of the subject is used as a medical image. However, brain images other than the MRI image, such as a CT image and a PET image, may be used.

Hereinafter, the effect of the present embodiment will be described.

By calculating the similarity between each of the plurality of standard brain images and each of the plurality of past brain images, it is possible to calculate the similarity with an appropriate standard brain image according to the subject. Therefore, it is possible to select a reference brain image that is more suitable for calculating the atrophy rate of the brain.

By acquiring the volume change amount from the corresponding region of the reference brain image in at least one region of the plurality of regions for the brain included in the target brain image, it is possible to accurately acquire the volume change amount of each region.

By performing the second registration after performing the first registration using landmarks, further registration is performed after registration using a region for which registration is easy, which is called a landmark, is performed. For this reason, it is possible to efficiently perform registration between the target brain image and the standard brain image.

By performing the fourth registration after performing the third registration using landmarks, further registration is performed after registration using a region for which registration is easy, which is called a landmark, is performed. For this reason, it is possible to efficiently perform registration between the target brain image and the reference brain image.

EXPLANATION OF REFERENCES

1: medical image processing apparatus
2: three-dimensional image capturing apparatus
3: image storage server
4: network
11: CPU
12: memory
13: storage
14: display
15: input unit
21: image acquisition unit
22: similarity calculation unit
23: selection unit
24: change amount calculation unit
25: division unit
26: registration unit
27: change amount acquisition unit
28: display control unit
31, 32: cerebral ventricle

40: region
41, 42, 43: pixel
B0: reference brain image
Bt: target brain image
Bpi: past brain image
Bs: standard brain image
Gt, G0, Gt1: slice image
L10, L11: label
Vm: movement vector

What is claimed is:

1. A medical image processing apparatus, comprising:
an image acquisition unit that acquires a target brain image as a diagnostic target and a plurality of past brain images, which have earlier imaging dates and times than the target brain image, for the same subject;
a similarity calculation unit that calculates a similarity between each of the plurality of past brain images and a standard brain image; and
a selection unit that selects a past brain image, which has the similarity equal to or greater than a predetermined threshold value and has an imaging date and time closest to a current date and time, as a reference brain image from the plurality of past brain images.

2. The medical image processing apparatus according to claim 1,
wherein the similarity calculation unit calculates a similarity between each of a plurality of standard brain images and each of the plurality of past brain images.

3. The medical image processing apparatus according to claim 1,
wherein the similarity calculation unit performs registration between each of the plurality of past brain images and the standard brain image, and calculates a correlation between the standard brain image and each of the plurality of past brain images after the registration as the similarity.

4. The medical image processing apparatus according to claim 2,
wherein the similarity calculation unit performs registration between each of the plurality of past brain images and the standard brain image, and calculates a correlation between the standard brain image and each of the plurality of past brain images after the registration as the similarity.

5. The medical image processing apparatus according to claim 1, further comprising:
a change amount calculation unit that calculates an amount of change of a brain based on the target brain image and the reference brain image.

6. The medical image processing apparatus according to claim 2, further comprising:
a change amount calculation unit that calculates an amount of change of a brain based on the target brain image and the reference brain image.

7. The medical image processing apparatus according to claim 3, further comprising:
a change amount calculation unit that calculates an amount of change of a brain based on the target brain image and the reference brain image.

8. The medical image processing apparatus according to claim 5,
wherein the change amount calculation unit comprises:
a division unit that divides a brain included in the target brain image into a plurality of regions by performing registration between the target brain image and the standard brain image;
a registration unit that performs registration between the target brain image and the reference brain image; and
a change amount acquisition unit that acquires an amount of change from a corresponding region in a brain included in the reference brain image, for at least one region of the plurality of regions in a brain included in the target brain image, based on a result of registration between the target brain image and the reference brain image.

9. The medical image processing apparatus according to claim 6,
wherein the change amount calculation unit comprises:
a division unit that divides a brain included in the target brain image into a plurality of regions by performing registration between the target brain image and the standard brain image;
a registration unit that performs registration between the target brain image and the reference brain image; and
a change amount acquisition unit that acquires an amount of change from a corresponding region in a brain included in the reference brain image, for at least one region of the plurality of regions in a brain included in the target brain image, based on a result of registration between the target brain image and the reference brain image.

10. The medical image processing apparatus according to claim 7,
wherein the change amount calculation unit comprises:
a division unit that divides a brain included in the target brain image into a plurality of regions by performing registration between the target brain image and the standard brain image;
a registration unit that performs registration between the target brain image and the reference brain image; and
a change amount acquisition unit that acquires an amount of change from a corresponding region in a brain included in the reference brain image, for at least one region of the plurality of regions in a brain included in the target brain image, based on a result of registration between the target brain image and the reference brain image.

11. The medical image processing apparatus according to claim 8,
wherein the change amount acquisition unit calculates a volume change amount from a corresponding region of the reference brain image for at least one region of the plurality of regions in the brain included in the target brain image.

12. The medical image processing apparatus according to claim 6, further comprising:
a display control unit that displays the volume change amount on a display unit.

13. The medical image processing apparatus according to claim 8,
wherein the registration unit acquires a movement vector between corresponding pixel positions as the amount of change between corresponding regions of the brain included in the target brain image and the brain included in the reference brain image.

14. The medical image processing apparatus according to claim 8,
wherein the division unit performs second registration between the target brain image and the standard brain image after performing first registration using landmarks between the target brain image and the standard brain image.

15. The medical image processing apparatus according to claim 14, wherein the first registration is registration by similarity transformation, and the second registration is registration by nonlinear transformation.

16. The medical image processing apparatus according to claim 8, wherein the registration unit performs fourth registration between the target brain image and the reference brain image after performing third registration using landmarks between the target brain image and the reference brain image.

17. The medical image processing apparatus according to claim 16, wherein the third registration is rigid registration, and the fourth registration is registration by nonlinear transformation.

18. A medical image processing method, comprising:

acquiring a target brain image as a diagnostic target and a plurality of past brain images, which have earlier imaging dates and times than the target brain image, for the same subject;

calculating a similarity between each of the plurality of past brain images and a standard brain image; and selecting a past brain image, which has the similarity equal to or greater than a predetermined threshold value and has an imaging date and time closest to a current date and time, as a reference brain image from the plurality of past brain images.

19. A non-transitory computer readable recording medium storing a medical image processing program causing a computer to execute:

a step of acquiring a target brain image as a diagnostic target and a plurality of past brain images, which have earlier imaging dates and times than the target brain image, for the same subject;

a step of calculating a similarity between each of the plurality of past brain images and a standard brain image; and a step of selecting a past brain image, which has the similarity equal to or greater than a predetermined threshold value and has an imaging date and time closest to a current date and time, as a reference brain image from the plurality of past brain images.

20. A medical image processing apparatus comprises:

a memory that stores commands to be executed by a computer; and a processor configured to acquire a target brain image as a diagnostic target and a plurality of past brain images, which have earlier imaging dates and times than the target brain image, for the same subject;

calculate a similarity between each of the plurality of past brain images and a standard brain image; and select a past brain image, which has the similarity equal to or greater than a predetermined threshold value and has an imaging date and time closest to a current date and time, as a reference brain image from the plurality of past brain images.

* * * * *